(12) United States Patent
Hainfeld et al.

(10) Patent No.: US 6,955,639 B2
(45) Date of Patent: Oct. 18, 2005

(54) METHODS OF ENHANCING RADIATION EFFECTS WITH METAL NANOPARTICLES

(75) Inventors: James F. Hainfeld, Shoreham, NY (US); Daniel N. Slatkin, Southold, NY (US)

(73) Assignee: Nanoprobes, Inc., Yaphank, NY (US)

( * ) Notice: Subject to any disclaimer, the term of this patent is extended or adjusted under 35 U.S.C. 154(b) by 0 days.

(21) Appl. No.: 10/387,059

(22) Filed: Mar. 12, 2003

(65) Prior Publication Data

US 2004/0181114 A1 Sep. 16, 2004

(51) Int. Cl.$^7$ ................................. A61N 5/00
(52) U.S. Cl. ........................... 600/1; 977/DIG. 1
(58) Field of Search .................... 600/1–15; 424/1.11, 424/497, 179.1, 1.29, 1.17, 1.65, 9.3; 264/473, 488; 514/44; 536/23.1, 24.5; 607/88, 100; 530/391.5; 436/525; 378/65; 435/173.5, 285.2, 2; 977/DIG. 1

(56) References Cited

U.S. PATENT DOCUMENTS

| | | | |
|---|---|---|---|
| 5,521,289 A | | 5/1996 | Hainfeld et al. |
| 6,001,054 A | | 12/1999 | Regulla et al. |
| 6,165,440 A | * | 12/2000 | Esenaliev ............... 424/1.11 |
| 6,369,206 B1 | | 4/2002 | Leone et al. |
| 6,530,944 B2 | * | 3/2003 | West et al. ............. 607/88 |
| 6,645,464 B1 | | 11/2003 | Hainfeld |

FOREIGN PATENT DOCUMENTS

WO  WO 00/06244  2/2000

OTHER PUBLICATIONS

Manuel H. Castillo, et. al., "Effects of Radiotherapy on Mandibular Reconstruction Plates", *The American Journal of Surgery*, vol. 156, pp. 261–263, (1988).
D. F. Regulla, et. al., "Physical and Biological Interface Dose Effects in Tissue due to X–Ray Induced Release of Secondary Radiation from Metallic Gold Surfaces", *Radiation Research*, vol. 150, pp. 92–100, (1998).
Indra J. Das, et al., "Backscatter dose perturbation in kilovoltage photon beams at high atomic number interfaces", *Medical Physics*, vol. 22, No. 6, pp. 767–773, (1995).
D. M. Herold, et. al. "Gold microspheres: a selective technique for producing biologically effective dose enhancement", *International Journal of Radiation Biology*, vol. 76, No. 10, pp. 1357–1364, (2000).
Hiromichi Matsudaira, et. al., "Iodine Contrast Medium Sensitizes Cultured Mammalian Cells to X Rays but not to Y Rays", *Radiation Research*, vol. 84, pp. 144–148, (1980).

* cited by examiner

*Primary Examiner*—Max F. Hindenburg
*Assistant Examiner*—Nikita R. Veniaminov
(74) *Attorney, Agent, or Firm*—Scully, Scott, Murphy & Presser

(57) ABSTRACT

The present invention provides methods of using metal nanoparticles 0.5 to 400 nm in diameter to enhance the dose and effectiveness of x-rays or of other kinds of radiation in therapeutic regimes of ablating a target tissue such as tumor. The metal nanoparticles can be administered intravenously, intra-arterially, or locally to achieve specific loading in and around the target tissue. The metal nanoparticles can also be linked to chemical and/or biochemical moieties which bind specifically to the target tissue. The enhanced radiation methods can also be applied to ablate unwanted tissues or cells ex vivo.

54 Claims, 2 Drawing Sheets

METHODS OF ENHANCING RADIATION EFFECTS WITH METAL NANOPARTICLES

FIELD OF THE INVENTION

This invention relates in general to methods of enhanced radiotherapy. In particular, the present invention relates to methods of enhancing the therapeutic effects of radiation in promoting the shrinkage and/or elimination of tissues targeted for destruction, e.g., tumors, by using nanoparticles of gold and/or other metals, without unacceptable damage to surrounding normal tissues.

BACKGROUND OF THE INVENTION

Radiation of various forms, for example x-rays, laser light, and microwaves, as well as particle beams of, for example, neutrons, electrons, and protons, have been used to treat tumors. Unfortunately, such radiations are not generally very specific for the tumor. Tumoricidal doses of radiation often results in serious damage to normal tissue, thus limiting irradiation to lower doses that are not curative.

Radiosensitizer compounds are drugs that act in combination with radiation to produce improved response, usually by making DNA more susceptible to radiation, or extending the life of free radicals produced by the radiation. Another type of radiation enhancer includes elements or compounds that interact directly with the radiation to cause more tissue damage by increasing the absorption or scattering of the radiation, causing more local energy deposition by production of secondary electrons, alpha particles, Auger electrons, ionizations, fluorescent photons, and free radicals, for example. For cancer therapy, the purpose is to selectively enhance dose to the tumor, so these drugs, elements or compounds must be preferentially accumulated in tumor tissue or the tumor tissue must respond in a preferential way, to spare normal tissue.

Some radiosensitizers are themselves anti-cancer chemotherapeutic drugs that appear to work synergistically with x-irradiation. For example, the drug etanidazole was found to enhance radiation-induced cell death in one cell type, but not in another. (Inanami O, Sugihara K, Okui T, Hayashi M, Tsujitani M, Kuwabara M., "Hypoxia and etanidazole alter radiation-induced apoptosis in HL60 cells but not in MOLT-4 cells," *Int J Radiat Biol* 78:267–74, 2002). Carboplatin, cisplatin, and oxaliplatin were found to enhance radiotherapy in a leukemia mouse model (Dionet C A, Rapp M, Tchirkov A, "Comparisons of carboplatin and cisplatin as potentiators of 5-fluorouracil and radiotherapy in the mouse L1210 leukaemia model," *Anticancer Res* 22:721–725, 2002; Cividalli A, Ceciarelli F, Livdi E, Altavista P, Cruciani G, Marchetti P, Danesi D T, "Radiosensitization by oxaliplatin in a mouse adenocarcinoma: influence of treatment schedule," *Radiat Oncol Biol Phys* 52:1092–1098, 2002).

Pre-irradiation exposure to some nucleic acid base derivatives, e.g., halogenated purines or pyrimidines, has been found to potentiate radiation treatment. Although the mechanisms are not completely understood, some data suggest that these bases may be incorporated into DNA or RNA leading to functional disruption, or that they may inhibit enzymes, such as thymidylate synthetase, thus disrupting DNA synthesis. Since gamma rays are believed to disable cell division by causing double-strand DNA breaks, DNA repair pathways are therefore important modulators of lethality. Inhibition of double strand break rejoining has been observed in human adenocarcinoma cells following protracted pre-irradiation treatment with 5-fluorodeoxyuridine. This effect appeared to be primarily related to the inhibition of thymidylate synthetase and the resulting perturbation of nucleotide pools in those cells (Bruso, C E, Shewach, D S, Lawrence, T S, *Int. J. Radiat. Oncol. Biol. Phys.* 19:1411–1417, 1990). 5-Fluorouracil is often used in combination with radiotherapy for the treatment of malignant tumors, particularly with rectal cancer (Buchholz, D J, Lepek, K J, Rich, T A, and Murray, D, *Int. J Radiat. Oncol. Biol. Phys.* 32:1053–1058; 1995). 5-iododeoxyuridine and 5-bromodeoxyuridine are being used in clinical trials, but have shown only limited efficacy. 5-chloro-2'-deoxycytidine co-administered with three biomodulators of its metabolism, N-(phosphonacetyl)-L-aspartate (PALA), tetrahydrouridine, and 5-fluoro-2'deoxyctidine, combined with fractionated x-ray treatments, produced improved results in test animal tumor models showing a threefold dose enhancement and a substantial number of cures (Greer, S, Schwade, J, and Marion, H S, *Int. J. Radiat. Oncol. Biol. Phys.* 32:1059–1069; 1995). These chemical methods of radiation enhancement are not widely used in standard clinical radiotherapy treatments because of the unpredictability and variability of response in different tumor types, the toxicity of the agents, and some disappointing clinical trials.

Photophrin and similar compounds have been found useful in treating some particular types of tumors. These compounds absorb visible light and result in formation of toxic free radicals. Direct cytotoxicity via intracellular damage can result from a type I mechanism where highly reactive free radicals are generated that can damage intracellular membranes and mitochondria, or a type II mechanism where excitation to reactive singlet oxygen species leads to oxidation of membranous cell structures. Ischemic necrosis can also result by vascular occlusion occurring secondary to vasoconstriction, platelet activation/aggregation, and intravascular thrombosis, which may be partly mediated by local release of thromboxane A2. A disadvantage of this phyotodynamic therapy (PDT) is that it requires visible (laser) light to penetrate the tumor and is thus limited to superficial tissue, or those tissues that are optically accessible, generally superficial malignancies. Uniformity of dose delivery is also a problem due to the high absorbance of the light by tissue. These restrictions limit the use of PDT to only a few tumor types and situations.

Another form of radiation enhancement studied is the use of boron-10-containing compounds that have a high cross section for absorption of neutrons. Upon neutron capture, boron fissions into a lithium ion and alpha particle which have ranges of 5–9 microns and can locally damage DNA and kill cells. This is called Boron Neutron Capture Therapy (BNCT). For example, see: Miura M, Morris G M, Micca P L, Lombardo D T, Youngs K M, Kalef-Ezra J A, Hoch D A, Slatkin D N, Ma R, Coderre J A,"Boron Neutron Capture Therapy of a Murine Mammary Carcinoma using a Lipophilic Carboranyltetraphenylporphyrin," *Radiat Res.*155:603–610, 2001. This method requires a costly source of slow neutrons such as a low-power nuclear reactor or a high-current of energetic protons impinging on a cooled lithium target. Moreover, the boron-containing compounds available so far to treat human tumors do not have extraordinary affinities for tumors. These factors have hindered widespread development and use of BNCT. Target nuclides other than $^{10}$B such as $^{157}$Gd have also been proposed for neutron capture therapy.

The second type of radiation enhancement, called photoactivation, involves the use of an element that has a higher absorption coefficient for x-rays than soft tissue, which results in increased local energy deposition. For example, iodine was used in a number of studies to load the nucleic acid with the iodine-containing nucleic acid base iododeoxyuridine (IudR). After incorporation into cellular DNA in vitro, irradiation resulted in a radiotherapeutic advantage of a factor of about 3 (Nath, R, Bongiomi, P, and Rockwell, S, "Iododeoxyuridine radiosensitization by low- and high-energy photons for brachytherapy dose rates," *Rad. Res.* 124:249–258, 1990). However, to achieve this, the cells were altered so that 22–45% of the thymine in their DNA had been substituted with IUdR. Unfortunately, this level of substitution is not practical in vivo, and it would be difficult to selectively make such changes only in tumor cells.

The dose enhancement of x-rays adjacent to high atomic number (high-Z) elements has been known for over 50 years. At least 20 years ago it was speculated that this effect, then noted in vitro, might be employed to enhance radiotherapy of cancer (Matsudaira, H., Ueno, A. M., and Furuno, I., "Iodine contrast medium sensitizes cultured mammalian cells to x-rays but not to γ rays," *Rad. Res.* 84: 144–148, 1980). Radiation oncologists have also noted tissue necrosis around metal implants following therapeutic irradiation with x-rays (Castillo, M H, Button, T M, Doerr, R, Homs, M I, Pruett, C W, Pearce, J I, "Effects of radiotherapy on mandibular reconstruction plates," *Am. J. Surg.* 156, 261 (1988)). Das and coworkers made careful measurements of the dose enhancement factor at low-Z/high-Z interfaces irradiated by x-rays (Das, I J, Chopra, K L, "Backscatter dose perturbation in kilovoltage photon beams at high atomic number interfaces," *Med. Phys.* 22: 767–773, 1995). Experimental x-ray dose enhancement adjacent to bulk metallic gold was reported by Regulla and coworkers (Regulla, D F, Hieber, L B, and Seidenbusch, M, "Physical and biological interface dose effects in tissue due to x-ray-induced release of secondary radiation from metallic gold surfaces," *Rad. Res.* 150, 92 (1998)). A solid state detector was placed next to a thin (150 $\mu$m) gold foil and a dose enhancement factor of more than 100 with a range of 10 $\mu$m was found in the range of 40 to 120 kV tube potential. Cells were then placed in close proximity (2 $\mu$m) to the gold surface. In a clonogenic assay, 80 keV x-rays caused 80% cell killing at 0.2 Gy, which was a factor of 50 over the control without gold.

U.S. Pat. No. 6,001,054 to Regulla and Eckhard discloses a method for treating a site in a human body to inhibit abnormal proliferation of tissue at the site by introducing a metal surface at the site and then directing ionizing irradiation to the metal surface to obtain locally enhanced radiation therapy. The metal surface can be solid, e.g., a metallic stent, which is placed in the blood vessels adjacent to the tissue to ablate. Unfortunately, it would be impractical to place bulk metal surfaces throughout all tumor vessels and tissues. The dose enhancement from the metal was observed within only about 100 microns of the stent. Therefore, a few stents in a tumor would not be enough to treat the whole tumor. The '054 patent also discloses that the metal surface can be composed of spaced apart particles which range in size from 5 $\mu$m to 100 $\mu$m in diameter and are incorporated with metal or metal ions. However, there is no showing of delivery of sufficient metal to the tumor by means of these particles for effective treatment. In addition, the form of radiation taught by Regulla is restricted to less than 400 keV, which could not treat tumors at depth. Although skin cancers might be treated using this photon energy range, such tumors are more readily removed surgically.

Herold et al. reported the use of 1.5–3.0 micrometer diameter gold particles (1% by weight) in a stirred suspension with living cells during irradiation with 100–240 kVp x-rays and found a dose enhancement factor from a clonogenic assay to be 1.54 (Herold, D M, Das, I J, Stobbe, C C, Iyer, R V, and Chapman, J D, "Gold microspheres: a selective technique for producing biologically effective dose enhancement," *Int. J. Rad. Biol.* 76: 1357–1364, 2000). They also injected these particles (1.5–3 micron in diameter, 1% gold suspension) directly into a growing tumor at 3 sites followed by irradiation (8 Gy, 200 kVp). No tumor remission or shrinkage in the animals was reported, but extracted cells from the tumor were found to have a 0.15 plating efficiency rather than the control value of 0.25. Histological examination showed gold particles predominantly in the interstitial fluid, and "no gold particles were found in zones of tightly packed tumor cells, suggesting that it would be difficult to achieve uniform delivery of particles . . . throughout a tumour volume by direct injection." Since the dose is only increased in about a 100 micron region around the gold, this method would leave many tumor cells without enhanced treatment. These investigators found the particles did not diffuse into the tumor but remained at the three sites of injection.

Prior to the present invention, there has been no report of effective treatment of tumors using radiation in combination with heavy metals. Nor has there been any attempt of using a nanoscale approach to selectively ablate the unwanted cells or tissue.

SUMMARY OF THE INVENTION

This invention relates to methods of enhanced radiation therapy for promoting the shrinkage and/or elimination of tissues targeted for destruction by using nanoparticles of gold and/or other heavy metals.

In particular, the present invention provides methods for enhancing the effects of radiation directed to a tissue or cells in or from an animal by administering an amount of metal nanoparticles to the animal or to the tissue or cells ex vivo, then irradiating the animal with radiation directed to the tissue or cells, or irradiating the tissue or cells ex vivo. The methods of the present invention are useful for ablating unwanted tissues in an animal without unacceptable damage to surrounding normal tissues or substantial toxicity to the animal.

In a preferred embodiment, the tissues or cells targeted for destruction are tumorous. Tumors which can be treated by the present methods include any solid tumors such as carcinomas, brain tumor, melanomas, lymphomas, plasmocytoma, sarcoma, glioma, thymoma, and the like. Other tumors which can be treated by the present methods include, e.g., tumors of the oral cavity and pharynx, digestive system, respiratory system, bones and joints, soft tissue, skin, breast, genital system, urinary system, eye and orbit, brain and other nervous system, endocrine system, myeloma, and leukemia.

Metal nanoparticles suitable for use in radiation therapy are composed of a metal core and typically a surface layer surrounding the metal core.

Metals which can be used to form nanoparticles suitable for enhancing radiation effects are heavy metals, or metal with a high Z number, including but not limited to gold, silver, platinum, palladium, cobalt, iron, copper, tin, tantalum, vanadium, molybdenum, tungsten, osmium, iridium, rhenium, hafnium, thallium, lead, bismuth, gadolinium, dysprosium, holmium, and uranium. A preferred metal is gold. The metal core can consist of one metal, or it can be a mixture or an ordered, concentric layering of such metals, or a combination of mixtures and layers of such metals.

According to the present invention, the size of the metal core should be in the range of 0.8 to 400 nm in diameter. It has been surprisingly found that nanoparticles of heavy metals of this size selectively increase the local radiation dose directed to a target tissue such as a tumor and do not exhibit substantial toxicity in the animal. Preferably, the metal core is of a size in the range of 0.8 to 20 nm in diameter; and more preferably, 0.8 to 3 nm in diameter.

The shell or surface layer material typically surrounding the metal can be molecules containing sulfur, phosphorus or amines, e.g., phosphines, phenanthrolines, silanes and organo-thiols. Other surface layer materials suitable for use in accordance with the present invention include synthetic polymers, proteins, antibodies, antibody fragments, peptides, nucleic acids, carbohydrates, lipids, drugs, and other compounds.

In a preferred embodiment, the nanoparticles for use in enhanced radiation therapy are gold particles of 1 to 3 nm in diameter with thioglucose molecules as the shell material.

In another embodiment, the present invention provides polyanions of metals complexed with quaternary ammonium salts for use in radiation enhancement.

In another preferred embodiment, the metal nanoparticles have been made to target specific tissues by incorporating in the shell material, or by linking or attaching the particles to, a molecule that has affinity for the target tissue. Such molecule can be an antibody, antibody fragment, single chain antibody, peptide, nucleic acid, carbohydrate, lipid, drug, or any other compound that binds to the target tissue. For example, metal particles are linked to peptides or antibodies that bind to angiogenic endothelial molecules such as the integrin $\alpha_v\beta_3$ receptor or members of the VEGF receptor tyrosine kinase family.

Radiation can be in the form of low energy (about 1 to 400 KeV) or high engery x-ray (about 400 KeV up to 25,000 KeV). Radiation can also be in the form of microbeam arrays of x-ray or radioisotopes. Other forms of radiation suitable for use in practicing the methods of the present invention include, but are not limited to, visible light, lasers, infrared, microwave, radio frequencies, ultraviolet radiation, and other electromagnetic radiation at various frequencies. Various sources or forms of radiation can be combined, particularly for treating tumors at depth.

In one embodiment of the present invention, the enhanced radiation therapy is applied to an animal such as a human individual, to ablate or destruct an unwanted tissue, e.g., a tumor. Metal nanoparticles can be administered to an animal prior to irradiation by standard methods, e.g., intravenous or intra-arterial injection, direct injection into a target tissue (e.g., tumor), and implantation of a reservoir device capable of a slow release of metal nanoparticles. In general, nanoparticles are administered in an amount to achieve a concentration in the animal of at least about 0.05 to 10% metal by weight, preferably 0.1 to 5% metal by weight, and more preferably 0.3% to 2% metal by weight, in order to achieve radiation enhancement.

In another embodiment, the enhanced radiation therapy is applied to tissues or cells ex vivo to ablate or destroy unwanted tissues or cells from an animal. For example, the enhanced radiation methods can be applied to bone marrow ex vivo to eliminate unwanted cells prior to transplantation, or applied to a donor organ to remove immunogenic cells prior to transplantation.

The enhanced radiotherapy methods disclosed herein can be used in conjunction with other existing therapies, such as chemotherapy, anti-angiogensis therapy and boron neutron capture therapy (or BNCT).

DETAILED DESCRIPTION OF THE INVENTION

Figure 1:
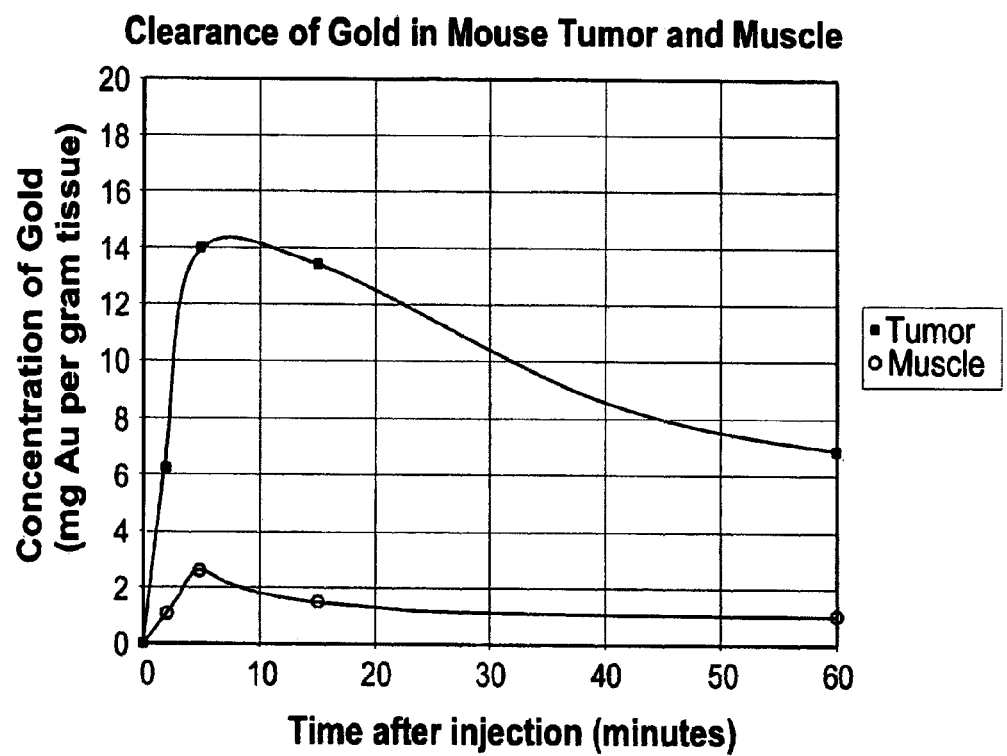
FIG. 1. Balb/C mice were implanted in their hindleg with the syngeneic mouse mammary tumor EMT-6. Gold nanoparticles 0.8 to 3 nm were injected intravenously into the tail vein. Mice were killed at various time points after gold injection and tissues analyzed for gold content by graphite furnace atomic absorption spectroscopy. At 5 minutes after injection, the bulk tumor contained an average of 14 mg gold per gram of tumor (1.4% gold by weight), and muscle contained 2.6 mg gold per gram of muscle. These data demonstrated a tumor to non-tumor (muscle) ratio of gold to be 5.4. It also demonstrated that therapeutic levels of gold can be delivered to tumors without any noticeable toxicity.

It has been surprisingly found by the present inventors that metal nanoparticles can selectively increase the local radiation dose to a tumor or tissue. More particularly, it has been surprisingly discovered that gold nanoparticles, e.g., gold particles of 0.8–3 nm in diameter, injected intravenously selectively accumulate in solid tumors. This unique recognition permits the use of gold nanoparticles for dose enhancement of radiation directed specifically to tumors, but not normal surrounding tissues. It has also been surprisingly discovered that gold nanoparticles, e.g., gold particles of 0.8–3 nm in diameter, injected intravenously remain in high concentration in tumors for 15 minutes or longer, whereas the blood concentration falls more rapidly. This differential loading of the particles in tumor is desirable for obtaining a selective dose enhancement effect in tumor. Moreover, it has been shown for the first time that tumors in animals were reduced in size and eventually disappeared after the injection of gold nanoparticles followed by irradiation. There are no serious long-term adverse effects observed in any of the animals treated and the gold nanoparticle agents used are well tolerated even at concentrations in the blood of up to 5% gold by weight, with no indication of toxicity to liver, kidneys or other organs. The hematology of the animals is also normal and the animals have normal levels of hemoglobin (Hgb), hematocrit (HCT), glucose (GLUCm), creatinine (CREm), blood urea nitrogen (BUN), total protein (TPm), albumin (ALBm), total bilirubin (TBIL), differential bilirubin (DBILm), gamma-glutamyl transferase (GGT), aspartate aminotransferase (AST, or SGOT for serum glutamic oxaloacetic transaminase), alanine aminotransferase (ALT), and alkaline phosphatase (ALP).

Based on these discoveries, the present invention provides methods for enhancing the effects of radiation directed to tissues or cells by irradiating the tissues or cells in the presence of metal nanoparticles. The methods of the present invention are useful for ablating unwanted tissues in an animal. The methods are also applicable to ex-vivo use to ablate tissues or cells, for example, in purification of bone marrow from unwanted cells before transplantation, or treatment of a transplant organ to remove immunogenic cells.

The term "animal" as used herein is taken to mean any mammalian subject, preferably, a human subject.

In accordance with the present invention, radiation is directed to a tissue or a population of cells targeted for destruction or ablation, also referred herein as a "target tissue" or "target cells". By "ablating a tissue or cell" is meant that the growth of the tissue or cell is inhibited, the size of the tissue or the number of the cells is reduced, or the tissue or cell(s) is eliminated.

In a preferred embodiment, the tissue or the population of cells targeted for destruction is a tumor or a population of cancerous cells. According the present invention, the enhanced radiation with metal particle is effective in treating any tumor which include, but are not limited to, tumors of the oral cavity and pharynx, digestive system, respiratory system, bones and joints, soft tissue, skin, breast, genital system, urinary system, eye and orbit, brain and other nervous system, endocrine system, lymphoma, myeloma, and leukemia. Preferably, the tumor targeted for destruction is a solid tumor such as carcinomas, brain tumor, melanomas, lymphomas, plasmocytoma, sarcoma, glioma, and thymoma.

By "treating a tumor" is meant that the tumor growth is significantly inhibited, as indicated by, e.g., a reduced tumor volume, or disappearance of tumor or tumorous cells.

In another embodiment, the target tissues or cells are non-tumorous and can include, e.g., hypertrophied tissue such as thyroid, bone (especially in cases of bone regrowth around joint replacements that prove problematic), epithelial or vascular tissues for control of restenosis after balloon angioplasty, atherosclerotic plaque, and other unwanted tissues that may be difficult or dangerous to remove by surgery.

By administering metal nanoparticles to an animal or to tissues or cells ex vivo prior to irradiation, the therapeutic effects of radiation is enhanced. By "enhanced" or "enhancing" is meant that a lower dose of irradiation is required to achieve efficacy (e.g., the target tissue is ablated or eliminated) with metal nanoparticles as compared to without metal nanoparticles; or, better efficacies are achieved by a given dose of irradiation with metal nanoparticles as compared to without metal nanoparticles.

In accordance with the present invention, solid tumors, or carcinomas, may be treated by administration of metal nanoparticles to the animals followed by irradiation. Metal particles are delivered to these tumors through the vasculature, by direct local application, or delivery from a reservoir. Some of the beneficial effects can result by preferential damage to tumor vasculature.

Additionally, disseminated tumors, such as metastatic tumors, uterine cancer, and tumors of the blood, bone marrow, and lymphatic tissue, including leukemias, myelomas, and lymphomas, may be treated with the enhanced radiation methods disclosed herein. In these cases, the cancerous cells are targeted directly with the metal nanoparticles before irradiation. For example, advanced uterine cancer is marked by dissemination of tumor cells throughout the peritoneal cavity, making surgery ineffectual. Metal nanoparticles can be coated with tumor-binding molecules as described herein, and administered into the peritoneal cavity. The tumor cells may be preferentially laden with heavy metal nanoparticles to an extent that enhances the dose these cells receive from irradiation relative to the surrounding non-tumor tissue, resulting in an improved response. A similar methodology can be used to administer the targeting metal nanoparticles to diseased lymph nodes, bone marrow, and blood.

According to the present invention, unwanted cells from a tissue of an animal can be ablated ex vivo by employing the enhanced radiation methods of the present invention. The tissue can be extracted or removed from the animal, combined or admixed with metal particles which bind the unwanted cells specifically, and subjected to irradiation in the presence of the metal particles.

For example, cancerous blood cells or otherwise diseased blood cells such as virally infected or malarial red cells, can be ablated or eliminated by combining the blood with metal nanoparticles that target such unwanted blood cells, then irradiating the blood. This procedure can be best accomplished by an extracorporeal shunt, where the blood is taken from a vessel to circulate outside the body, where it is irradiated, then returned to the circulation. This prevents the radiation from impinging on other normal tissue.

As another example, unwanted cells in bone marrow or lymphoid tissue can be ablated or eliminated by extracting bone marrow or lymphoid tissue from a patient, then combining the extracted bone marrow or lymphoid tissue with the metal nanoparticles which are made to preferentially target an unwanted cell population, followed by irradiation to preferentially kill the unwanted cells. Meanwhile, the patient is irradiated to remove all other stem cells from like tissue. The externally purged extract is then used to replenish the bone marrow or lymphoid tissue. This method may be used to treat diseases of the bone marrow or lymphoid tissue, such as leukemias, lymphomas, myelomas, and autoimmune diseases such as multiple sclerosis and Lupus.

In still another example, the enhanced radiation methods are applied to ablate atherosclerotic plaque. Atherosclerotic plaque is a large public health problem resulting in heart attacks and strokes. Prior to the present invention, there is no effective method to remove the plaque from the vasculature. According to the present invention, metal nanoparticles are introduced into the vasculature of the plaque and the plaque itself, followed by irradiation to ablate the plaque tissue. Preferential accumulation into the plaque tissue may be passive due to the higher vascularity of the plaque tissue than surrounding tissue(s) and higher extravasation of nanoparticles. Alternatively, the metal nanoparticles may be actively targeted to the plaque, for example by using antibodies or peptides on the nanoparticles to direct them to foam cells or lipophilic particles that preferentially accumulate in plaque lipids.

For clarity of disclosure, and not by way of limitation, the detailed description of the invention is divided into the following subsections which describe or illustrate certain features, embodiments or applications of the invention.

Metal Particles:

It has been surprisingly found that metal nanoparticles of certain sizes are substantially non-toxic for safe administration to animals and can greatly enhance the effects of radiation therapy.

Metal particles or metal nanoparticles are composed of a metal core and typically a surface layer surrounding the metal core. The metal core of the particles is a cluster of metal atoms. Metal particles and nanoparticles can be made using techniques known in the art, e.g., those described in U.S. Pats. No. 5,521,289 and 6,369,206, the teachings of which are incorporated herein by reference. For example, gold particles are formed by reducing a gold ion source with a reducing agent such as phosphorus, borane, citrate, sodium borohydride, ionizing radiation, alcohol, aldehyde, or other reducing agent.

The size of the metal core can be controlled by using a certain type of reducing agent, including additional components in the reduction reaction that affect particle size, or altering the amounts and concentration of component reagents. Alternatively, the size of the metal core can be controlled by taking a small completed nanoparticle and depositing additional metal by autometallography.

In accordance with the present invention, the size of the metal core of nanoparticles suitable for use in radiation therapy is in the range of about 0.8 to 400 nm in diameter. Preferably, the core is of a size in the range of about 0.8 to 20 nm in diameter; and more preferably, about 0.8 to 3 nm in diameter.

Metals which can form nanoparticles suitable for use in enhancing radiation effects are heavy metals. The term "heavy metals" or "or high Z elements" as used herein refer to metal elements with an atomic number of at least 22, including but not limited to gold (Z=79), silver (Z=47), platinum (Z=78), palladium (Z=46), cobalt (Z=27), iron (Z=26), copper (Z=29), tin (Z=50), tantalum (Z=73), vanadium (Z=23), molybdenum, tungsten (Z=74), osmium (Z=76), iridium (Z=77), rhenium (Z=75), hafnium (Z=72), thallium (Z=81), lead (Z=82), bismuth (Z=83), gadolinium (Z=64), dysprosium (Z=66), holmium (Z=67), and uranium (Z=92).

A preferred choice of metal is gold. Gold has the ability to form a range of sizes in the nanometer and micron size range, and is relatively inert and substantially non-toxic.

In accordance with the present invention, the metal core can consist of one metal such as gold, silver, iron, platinum, palladium, iridium, tungsten and others listed above. Alternatively, the metal core can be a mixture or an ordered, concentric layering of such metals, or a combination of mixtures and layers of such metals. For example, alloys can be formed during synthesis by having two or more metal sources available for reduction. Alternatively, the metal core can be composed of two or more concentric shells of different metals. These are produced by forming the central metal particle, then depositing on it an additional layer of a different metal by electroless plating. Electroless plating, or autometallography, or metal enhancement, is performed by combining the starting metal particles with a source of ions of the same or a different metal and a reducing agent. The starting metal particles act catalytically to accelerate metal deposition from the solution, as opposed to extraneous metal deposition caused by autonucleation. By supplying only limited amounts of reducing agent or metal ions, the thickness of the metal coating can be controlled. Varying the time of the reaction is another way to control the deposited amount.

Alloyed or layered metal particles have a number of advantages over nanoparticles of one metal. For example, alloyed or layered metal particles may have better pharmacokinetic characteristics. The toxicity of a more toxic metal can be controlled by coating or alloying with another metal that is non-toxic. For example, lead nanoparticles can be coated with a chemically inert and non-toxic layer of gold. In additional, because various metals interact with radiation differently, a wider range of choices for enhancement of dose is available with alloyed or layered metal particles. Moreover, other metals may be less expensive than gold, making some choices more commercially attractive.

In accordance with the present invention, non-metal elements can also be present in the metal core, such as silicon, oxygen, and phosphorus. An example is the metal heteropolytungstate, $W_{12}O_{42}Si$.

The metal core is typically surrounded by a surface or shell layer of another material that is either covalently bound to the core or held to the core by non-covalent forces such as charge, hydrophobic, van der Waals interation, or a combination thereof.

Surface layer materials suitable for use in accordance with the present invention include molecules containing sulfur, phosphorus or amines, e.g., phosphines, phenanthrolines, silanes and organo-thiols, since sulfur, phosphorus and amines can form bonds with surface metal atoms. The thiol group can be linked to a sugar compound, such as glucose, a sugar oligomer or polymer.

Other surface layer materials suitable for use in accordance with the present invention include synthetic polymers, proteins, antibodies, antibody fragments, peptides, nucleic acids, carbohydrates, lipids, drugs, and other compounds, which can bind to the metal core by non-covalent interactions such as charge, hydrophobic or van der Waals interactions, or bind to the metal core by covalent interactions.

The surface layer material can be present during the reduction process or pre-attached to metal atoms, either becoming incorporated into the shell in situ or being added after the metal particle is formed. Alternatively, a metal nanoparticle with a first surface layer material is formed, which then exchanges some or all of the surface material with a second surface material. This exchange process may in some cases be hastened by heating in the presence of excess second shell material. Metal particles with the original shell material or the second shell material can be linked via chemical reactions to virtually any other molecule desired, be it a lipid, antibody, carbohydrate, nucleic acid, peptide polypeptide, drug or synthetic molecule.

The shell layer contributes to many of the particle's properties, such as solubility, toxicity, affinity, and pharmacokinetics (biodistribution in animals as a function of time). For example, it is known that gadolinium ions are highly toxic, but when complexed with an organic shell of DTPA (diethylenetriaminepentaacetate), they are non-toxic, and commonly used as a MRI contrast agent.

In a preferred embodiment of the present invention, gold particles of 1 to 3 nm in diameter with thioglucose molecules as its organic shell material are used in radiation enhancement. According to the present invention, these gold nanoparticles have a number of features that are desirable for in vivo therapeutic use. For example, it has been surprisingly found that these gold nanoparticles have very high serum solubility, accumulate specifically in the tumor and reside in tumors longer than in the blood or muscle. It has also been found that these gold nanoparticles are substantially non-toxic, have very low liver accumulation and are eliminated from the body predominantly through the kidney.

In another embodiment, the present invention provides polyanions of metals complexed with quaternary ammonium salts or covalently coated with an appropriate surface layer material for use in radiation enhancement. Polyanions are nanoparticle structures or metal-oxygen clusters formed by metals such as tungsten, vanadium, and molybdenum in an aqueous solution, which are characterized by metal-oxygen bonds rather than metal-metal bonds typical of nanoparticles of gold, silver, platinum, and palladium. Such polyanion particles are also referred to as heteropolyanions where a mixture of elements are present. An example of heteropolyanions is $M_{12}O_{42}X^{n-}$, where M=V, Mo, or W, and X=Si, P, V, Co, or B, and n>1. Other larger stable clusters are known such as ones containing $M_{18}$ and $M_{30}$. Unfortunately, these heteropolyanions compounds are toxic at levels useful for radiation enhancement. It has been surprising found by the present inventors that heteropolyanions complexed with quaternary ammonium salts are stable forms that are tolerated in vivo, and are therefore useful and safe for use in enhancing the effects of radiation therapy. Without intending to be bound by any particular theory, it is postulated that toxicity of heteropolyanions is at least in part due to the high negative charge of these clusters. Forming a complex with quaternary ammonium salts can shield such high charge and thus reduce the toxicity of heteropolyanions.

In another preferred embodiment, metal nanoparticles made to target specific tissues are employed in the radiation enhancement methods of the present invention. A nanoparticle can be made to target specific tissues by incorporating in the shell material, or by linking or attaching the particle to, a molecule that has affinity for the target tissue. Such molecule is also referred to herein as a "targeting molecule", or a "targeting moiety" or a "targeting ligand", which can be an antibody, antibody fragment, single chain antibody, peptide, nucleic acid, carbohydrate, lipid, drug, or any other compound that binds to the target tissue.

Nanoparticles containing a targeting molecule can be made in several ways. For example, a targeting molecule can be incorporated in a nanoparticle during the synthesis of the nanoparticle. Synthesis generally involves a reduction step where metal ions are reduced to form the metal core. The metal core is then capped with a surface layer material present in the solution, such as citrate ions, thiol-containing molecules, phosphines, phenanthrolines, and silanes. Peptides containing cysteine and Fab' antibody fragments that contains a free hinge thiol group, when used as a surface layer material, can bind covalently to surface metal atoms through the sulfur atom. Lectin that is covalently attached to a phosphine, when included in the synthesis step as surface layer material, binds covalently to surface metal atoms through the phosphine group.

Alternatively, a targeting molecule is attached to a metal naoparticle after the metal nanoparticle has been produced, under conditions where the targeting molecule replaces a pre-existing surface layer material. For example, thiol-containing molecules can replace some surface layer materials of metal nanoparticles. The kinetics of this exchange process is determined by the concentrations and binding affinities of the two surface materials, and heating can accelerate the process. Polymers, proteins, and other molecules can displace citrate ions and become attached to the metal particle surface via covalent interactions (e.g., through a sulfur or phosphorus atom) and/or non-covalent interactions, such as van der Waals, hydrophobic interactions, and charge attractions. Large molecules, such as proteins, generally bind to metal surfaces by multipoint non-covalent interactions, and are considered "adsorbed" to the metal particle.

Additionally, a targeting molecule can be linked to a metal nanoparticle in a chemical reaction through a chemically reactive group present in the targeting molecule and/or the surface layer material of the nanoparticle. For example, a gold nanoparticle that has a surface layer of phosphine where one or more of the phosphines contain a primary amine can react with a peptide that contains an N-hydroxysuccinimide ester, forming a covalent bond. A large number of cross-linking molecules are also available that enable linking of two molecules via their reactive groups.

In a preferred embodiment, metal particles are made to contain or are linked to peptides or antibodies that bind to angiogenic endothelial molecules such as integrin ($\alpha_v\beta_3$ receptor), VEGF receptor tyrosine kinases, including VEGF-R1 (Flt-1), VEGF-R2 (or "Flk-1" for murine and "KDR" (kinase domain receptor) for humans), and VEGFR-3. For example, antibody LM609 and a peptide containing the classical integrin-recognition motif Arginine-Glycine-Aspartic acid (RGD), both bind to the integrin $\alpha_v\beta_3$ receptor (Brooks, P. C. et al., "Antiintegrin alpha v beta 3 blocks human breast cancer growth and angiogenesis in human skin", *J. Clin. Invest.*1995, 96: 1815–1822). Peptides containing RGD and peptides containing the firbonectin NDR motif have been found to bind tumors in vivo (Arap W, Pasqualini R, Ruoslahti E., "Cancer treatment by targeted drug delivery to tumor vasculature in a mouse model", *Science.*1998, 279: 377–380). Such antibodies and peptides can be linked to metal particles and target these particles to angiogenic endothelium.

Administration

Metal nanoparticles can be combined with a pharmaceutically acceptable carrier. As used herein, a pharmaceutically acceptable carrier includes solvents, dispersion media, isotonic agents and the like. Examples of carriers include water, saline solutions, sugar, gel, porous matrices, preservatives and the like, or combinations thereof.

According to the present invention, metal nanoparticles prepared in accordance with the present invention can be administered to an animal for radiation enhancement by standard methods, including but not limited to intravenous or intra-aretrial injection, direct injection into a target tissue (e.g., tumor), and implantation of a reservoir device or cavity capable of a slow release of metal nanoparticles.

Intravenous injection is well suited to delivery of metal nanoparticle to the vascular system of an animal, and is a preferred method of administration where the target tissue to be ablated is a tumor. It has been surprisingly found by the present inventors that intraveonous injections of the gold nanoparticles attained temporally sustained higher concentrations in tumors over surrounding normal tissues. Without intending to be bound by any particular theory, it is believed that the longer residence time of nanoparticles in tumors may be due at least in part to the abundant vascularization of tumors. Intravenous injection also permits antibodies and peptides to directly reach their angiogenic targets at the tumor site. In accordance with the present invention, metal nanoparticles in the blood, especially those of 0.8–4 nm in diameter, may also penetrate the endothelial barrier of blood vessels. Tumor cells typically release Vascular Endothelial Growth Factor (VEGF), which stimulates endothelial growth, but also makes the vascular lining more permeable to small molecules. Nanoparticles which extravasate from the vasculature are believed to reach the extracellular compartment of the tumor parenchyma initially, and then possibly enter the intracellular compartment via endocytosis or other cell uptake mechanisms. Nanoparticles can be made to have a specific surface layer material that is capable of mediating specific uptake by malignant cells.

Direct intratumoral or tissue injection may be preferred in order to reduce the concentration of metal nanoparticles in other tissues and achieve a high concentration in the tumor or tissue to be ablated. Use of small nanoparticles, e.g., 0.8 to 10 nm in diameter, facilitates diffusion of the particles throughout the parenchyma of the targeted tissue. Linking nanoparticles to a specific targeting molecule can facilitate localization of the nanoparticles to specific cells, as disclosed hereinabove.

In some cases it may be advantageous to implant a reservoir of the metal nanoparticles adjacent to or in the bed of a target tissue. The reservoir can be a permeable bag or container, or a wafer, string, gel, Matrigel, or other material preloaded with the nanoparticles, or a time release pump driven osmotically, mechanically, or electrically. Once implanted, the metal nanoparticles can diffuse outward and, if the particles have a targeting moiety such as antibodies, peptides or other targeting substances, the particles can selectively bind to the cells of interest. Such reservoir administration has a number of attractive features. For example, a high concentration of nanoparticles can be achieved in the area of interest with minimal delivery to other tissues. The nanoparticles can be delivered over a controlled time period, and longer exposure to the nanoparticles may be achieved as compared to administration by intravenous injection. In addition, an almost "infinite" local supply is available for high loading to targets. The high concentration of metal in the reservoir does not significantly interfere with radiation treatment, since the metal dose enhancement only has a range of ~100 microns. Moreover, slow diffusion to track down and bind to locally disseminating or migrating tumor cells can be achieved. Alternatively, the metal nanoparticles can be placed in a body cavity which would also serve as a reservoir. Examples of body cavities include the bladder, peritoneal cavity, and brain ventricles.

In accordance with the present invention, reservoir administration of nanoparticles can be applied to an animal having a brain tumor. For example, a reservoir of metal nanoparticles can be inserted into the vacant space after the brain tumor is surgically debulked. Tumor cells can migrate away from the tumor mass, for even up to 3 cm or more, making complete surgical removal impossible. A reservoir of metal nanoparticles that are designed to target and bind to tumor cells can reach those cells which are not removed by surgery and can be killed by subsequent radiation treatment.

Amount of Metal and Dose Enhancement

Photons (e.g., x-rays) lose energy as they pass through matter. This occurs via three basic processes: Compton scattering, the photoelectric effect, and pair production.

In Compton scattering, photons collide with electrons, like billiard balls (an elastic collision), and energy and momentum are conserved. The impacted electron (recoil electron) can do chemical damage by creating an ion or further interacting with other local atoms. This interaction is proportional to the number of electrons the beam sees, i.e., the electron density of the material, and therefore varies depending on the atomic number (Z). As gold has a Z of 79 and soft tissue has a Z number similar to that of water (Z=7.4), the relative effect of a photon beam on gold versus tissue would be 10.7. Compton scattering is the dominant attenuation process in materials of low Z in the range of about 0.1 to 1 MeV.

The photoelectric effect is where an incident photon ejects an electron from the material, whereby energy from the beam is transferred into kinetic energy of the electron. This effect varies approximately as $(Z/E)^3$, where E is the incident photon energy. The relative effect of gold to tissue is then about 1217 ($79^3/7.4^3$) The photoelectric effect dominates at energies <1 MeV for high Z elements.

Pair production occurs at high photon energies (>>1 MeV), where the incident photon energy exceeds twice the rest mass of the electron (1.02 MeV), resulting in creation of electron-positron pairs (each having an energy of 0.511 MeV). This effect varies as $Z^2$, so the relative effect of gold to water is approximately 114 ($79^2/7.4^2$).

Accordingly, while it is clear that a radiation enhancement effect exists with photons of all energies levels, the photoelectric effect dominated region of the incident photon radiation energy spectrum would be the most advantageous for metal enhanced dose deposition.

According to the present invention, an estimated dose enhancement by metal can be determined based on the empirical absorption coefficients at different energies measured for tissue, gold and other metals. Specifically, attenuation in a material is given by:

$$I/I_o = \exp(-\mu\rho x) \qquad \text{(equation \#1)}$$

where I is the transmitted intensity, $I_o$ is the initial intensity, $\mu$ is the mass attenuation coefficient, $\rho$ is the density of the material and x is the thickness. Some of the scattered photons escape the local volume in other directions, attenuating the beam, but their energy is not fully absorbed. A more useful parameter for this discussion is $\mu_{en}/\rho$, which is the mass energy absorption coefficient, and which quantifies the energy actually deposited in the local volume. Tables available from National Institute of Standards and Technology, which are accessible by the public, plot $\mu_{en}/\rho$ for gold and soft tissue vs. energy. By dividing the entry in one graph by the corresponding entry in the other graph, the enhancement value for gold versus photon energy can be plotted. The resulting plot peaks at ~38 keV with an enhancement value of 160.

The peak gold to tissue absorption ratio of 160 means that for equal weights of gold or tissue, 160 times more energy is absorbed by the gold. In the context of the present invention, gold particles generally only make up a small fraction of the target tissue. The dose enhancement factor ($F_D$) would then be:

$$F_D = 1 + f_{Au} * (\mu_{en}/\rho)_{Au}/(\mu_{en}/\rho)_{st} \qquad \text{(equation \#2)}$$

where $f_{Au}$ is the fraction by mass of gold, $(\mu_{en}/\rho)_{Au}$ is the mass energy absorption coefficient for gold, and $(\mu_{en}/\rho)_{st}$ is the mass energy absorption coefficient for soft tissue. For example, a tissue loading of 0.31% gold by weight would give an enhancement in dose by a factor of 1.5:

$$F_D = 1 + 0.0031 * 160 = 1.5 \qquad \text{(equation \#3)}$$

The amount of gold particles per cell required to achieve this amount of loading can be determined as follows. A 15 nm diameter gold particle has a volume of $1.77 \times 10^{-18}$ cm$^3$ and a mass of $3.41 \times 10^{-17}$ g (density of gold is 19.3 g/cm$^3$). If an average cell has a diameter of 8 $\mu$m, its volume is then $2.68 \times 10^{-10}$ cm$^3$ and weight $2.68 \times 10^{-10}$ g (density 1 g/cc). A gold content of 0.31% by weight corresponds to $2.44 \times 10^4$ gold particles per cell.

The foregoing analysis provides some general guidance for getting numerical estimates of expected enhancements and by no means limits the scope of the present invention. It should be recognized that the actual dose enhancement value may depend on multiple factors, e.g., the complex nature of scattering, microdistribution or localization of the nanoparticles, the animal's responses (e.g., immune response, inflammatory response, clotting response, alterations in cytokine levels, and the like).

As a general rule, nanoparticles of one or more high Z elements are administered in an amount to achieve a concentration in the animal of about 0.05 to 10% metal by weight, preferably 0.1 to 5% metal by weight, and more preferably at least about 0.3% to2% metal by weight, in order to achieve radiation enhancement. Similarly, nanoparticles of one or more high Z elements are admixed with a tissue ex vivo in an amount to achieve a concentration in the mixture of about 0.05 to 10% metal by weight, preferably 0.1 to 5% metal by weight, and more preferably at least about 0.3% to 2% metal by weight, in order to achieve radiation enhancement ex vivo.

Radiation

Radiation can be in the form of x-rays. A number of interactions occur when a high Z material is subjected to x-rays. The primary beam can interact with the nucleus or electrons of the high Z material. The interactions can be in the form of Compton scattering, Rayleigh (elastic) scattering, pair production, the photoelectric effect, or a combination thereof.

In one embodiment of the present invention, the radiation source is a low energy x-ray of less than 400 keV.

The choice of the radiation energy can be determined taking into consideration various factors including, e.g., the type and location of the target tissue. It is recognized in the art that, with low energy x-rays (e.g., less than 100 keV), the photoelectric effect is the predominant form of interaction, and the interactions with high Z materials are substantially stronger as compared to those with tissue materials which typically have a low Z number. With higher energy x-rays, the differential effects of the radiation (i.e., high Z elements v. tissue) may be less significant; yet such higher energy sources provide energy which may permit electrons, ejected from the K or L shell of the high Z element, to traverse adjacent cells and impart a damaging effect. For example, the present inventors have found that x-rays of about 250 kVp (where "p" stands for the peak, or greatest photon energy) used in conjunction with gold nanoparticles has a stronger killing effects on tumor cells in vitro than a radiation source of about 100 kVp. However, for x-rays with energy levels far above the K or L shell excitation energy (e.g., >400 keV), the cross-section for creating a photoelectron diminishes.

In another embodiment of the present invention, the radiation source is a high-energy x-ray of at least about 400 KeV and up to about 25,000 keV.

According to the present invention, such high-energy x-rays are particularly useful for treating a target tissue deep (e.g., (~8–11 cm) below the body surface. Traditionally, such high-energy x-rays are not a desirable option in implementing high Z dose enhancement radiation therapy, because the absorption coefficient differences between the high Z material and tissue are believed to be much smaller than for low energy photons. However, the present inventors have uniquely recognized that a higher energy photon beam degrades as it progresses into tissue, resulting in a lower energy component and secondary low energy particles generated from the tissue, including secondary electrons, fluorescent photons, Auger electrons, and the like. The low energy components and particles can then interact in a more favorable way with the high Z material, giving a greater differential effect to the high Z material vs. tissue.

In still another embodiment, microbeam arrays of x-rays, now typically produced at synchrotrons, are used in practicing the methods of the present invention. Microbeam arrays or "microbeams" are beams of radiation that have been segmented into stacked sheets with no incident radiation between them. This is usually accomplished by taking a collimated source and passing it through a multislit collimator consisting of alternating transparent and opaque lines, much like the bars of a jail cell. However, the width of the microbeams is typically 20–80 microns wide, and the "dead space" between them is typically 50–800 microns wide. This form of radiation has been shown to spare normal tissue while being damaging to tumors. Having gold or a high Z material in the tumor would accentuate the microbeam effect.

In another embodiment, radioactive isotopes are used as the radiation source in conjunction with nanoparticles in cancer treatment or in other applications of tissue ablation. For example, isotopes of iodine (typically I-125, $t_{1/2}$=60.1 days palladium-103, $t_{1/2}$=17 days, or cesium-137) can be packaged into small metal tubes or "seeds" (typically about 5×0.5 mm) and implanted next to brain, prostate or other tumors. These implants provide radiation locally over a period related to the isotope's half-life. This implant approach is also referred to as "brachytherapy".

Iridium-192 has a high specific activity and has also been used in brachytherapy. High dose rate (HDR) Ir-192 seeds are fed through catheters, which are placed in and around a tumor. Because the dose rate is so high, the complete treatment is over in several minutes. According to the present invention, HDR Ir-192 is of particular utility in the context of the present invention. For example, gold nanoparticles can be administered intravenously and maximally accumulate in tumors in approximately 1 to 10 minutes. Use of a HDR source with a short irradiation would therefore be better matched to the residence time and maximum gold uptake time in a tumor, as compared to the use of I-125 which irradiates over several weeks.

Other useful radioactive isotopes can also be used to favor particular results. An isotope may be chosen so that the energy of its emitted gamma ray (or other emission) has a particularly high cross section of absorption with the high Z material compared to the low-Z of tissue. For example, xenon-133 ($t_{1/2}$=5.3 days) has an abundant (35%) gamma emission at 81 keV that is just above the K-edge of gold (80.7 keV). Thus, additional enhancement may be gained by exploiting the increased absorption above the discrete electron binding energies of the high-Z element.

Other forms of radiation suitable for use in practicing the methods of the present invention include, but are not limited to, visible light, lasers, infrared, microwave, radio frequencies, ultraviolet radiation, and other electromagnetic radiation at various frequencies. Various other sources may be employed, including, but not limited to: electrons, protons, ion beams, and neutrons. Many of these sources produce secondary effects that can be useful for the intended purpose of ablating a target tissue, for example, specific heating caused by energy absorption of the sample. A preferred gold nanoparticle solution disclosed herein is black in color and has a high extinction coefficient of absorption (about $1 \times 10^5$/M at 420 nm). It absorbs visible, ultraviolet, and infrared light particularly well, and enhances the effects of radiation absorption when present in a local vicinity that is irradiated, resulting in tissue-specific heating, for example.

Forms of Radiation for Treating Tumors at Depth

The use of low energy x-rays (10 to 400 keV, or even up to 1 MeV) in conjunction with nanoparticles may not be effective in treating tumors or ablating tissues at depth (2 to 10 cm below the body surface). X-rays in this range are significantly attenuated when penetrating tissue. For example, the intensity of the incident beam is attenuated to one-half of its value at 0.13 cm for 10 keV, 3.06 cm for 50 keV, 4.09 cm for 100 keV, 6.59 cm for 400 keV, and 9.89 cm for 1 MeV. Dose enhancement by metal nanoparticles may not be sufficient to compensate for the attenuation, since arbitrarily raising the dose may result in unacceptable doses at the skin and superficial tissues where the beam enters.

Accordingly, the metal nanoparticles are used preferably in conjunction with one of the following approaches of radiation to effectively treat tumors at depth.

Intraoperative Radiation—Radiation can be given during surgery when the patient's internal deep tumor is exposed, where the gold nanoparticles may be effectively irradiated by an x-ray source in the 25 to 1,000 keV range positioned near the tumor.

Brachytherapy—In this approach, small "seeds" of encapsulated radioactive material are placed in or adjacent to the tumor, thereby avoiding radiation at an excessive skin dose.

Insertable miniature x-ray tubes—Such x-ray tubes, which are commercially available, can be inserted into deep tissues, even brain tumors. For example, an x-ray tube source (50 keV max, 40 $\mu$a, 13 Gy/min) inside a thin, minimally invasive, needle-like probe (10 cm×3.2 mm) can be placed in almost any body tumor or region delivering a therapeutic dose in 0.5 to 30 min. These or similar sources of radiation could also be used with laparoscopy to access deep tumors.

Conformational irradiation—In this strategy, radiation is applied from multiple directions to produce a higher cumulative dose at the intersection of these beams at the tumor, referred to simply as "crossfired" or, in a more sophisticated embodiment, as amplitude-modulated conformal radiotherapy.

Grid Radiotherapy—In this approach, the beam is segmented into regions of centimeters to millimeters (using a metal sieve or grid, so that the beam is "on" in regions, but "off" in adjacent regions). This approach can reduce skin damage, particularly damage caused by orthovoltage sources which typically emit x-rays in the range of 100–500 kVp.

Microbeam Radiation—This form of x-ray irradiation extends the grid radiotherapy technique to the micron range, where the beam is segmented on the micron scale, typically 27 micron longitudinal beams separated by 73 microns of no beam, in a repeating pattern. This is currently implemented on a synchrotron using a multislit collimator, and with ~100 keV photons has been shown to greatly spare skin, and to deliver therapeutic doses to deep tumors with no serious normal tissue damage.

High-energy photons—X-rays in the 2 MeV to 30 MeV range have greater penetration and avoid excessive skin dose. The primary beam produces lower energy electrons and photons upon interaction with the tissue, and these secondary effects build up until a nearly steady state is achieved with depth. Since tissue damage is largely due to the secondary electrons and photons, these are not at high levels at skin entry point, thus avoiding skin damage. The primary energy may be adjusted to give the greatest effect to a tumor at depth. Many of the secondary electrons and photons produced are in an energy range that allows them to interact strongly with metals. Therefore, use of high-energy photons may be combined with metal nanoparticle dose enhancement for improved treatment of tumors at depth.

Advantages Over Other Treatment Modalities

Radiation therapy remains one of the most highly used treatment modalities for cancer. The use of metal nanoparticles in radiation, as disclosed in the present invention, effectively enhances the cancer-killing effects of irradiation. With the enhancement by metal nanoparticles, a lower dose may be required to cure or palliate cancer in a patient. Patients who otherwise do not completely respond to a maximum allowable dose of radiation may now have a better response. The enhanced radiation methods of the present invention also achieve a selective deposition of energy to tumor site thereby avoiding damage to normal tissue.

The enhanced radiotherapy methods as disclosed herein have particular advantages over many existing therapies. For example, chemotherapy generally employs a toxic drug to kill cancerous cells. As the drug can be toxic to normal cells throughout the body, the dose of the drug given must be limited. Unfortunately the whole body dose is often below the dose necessary to be curative. In the enhanced radiation methods of the present invention, while the metal nanoparticles are administered either locally or systemically, the radiation is directed only to a specific target tissue (e.g., the tumor site). Even if there is any accumulation of the metal nanoparticles in tissues (e.g., kidneys) other than the target site (e.g., a tumor in the brain), the metal particles themselves are not toxic. The damage to tissue is created only upon irradiation, and is therefore localized in and around the target tissue intended to be ablated. Thus, metal particles can be administered in higher amounts than toxic agents employed in chemotherapy.

The enhanced radiotherapy methods of the present invention are also advantageous over anti-angiogenesis therapy. Angiogenic inhibitors may cut off the supply of blood required by a tumor by suppressing the new growth of blood vessels. However, cells at the periphery of a growing tumor can obtain nutrients from normal vessels outside of the tumor site and continue to grow. In contrast, the metal particle/irradiation approach of the present invention can effectively eliminate these peripheral cells and blood vessels. Additionally, there are many angiogenic molecules, and therapies targeting only one or a few of these molecules may slow the angiogenesis process, but not eliminate it. The metal particle/irradiation approach, on the other hand, can effectively destroy both tumor cells and endothelial cells. A further disadvantage of anti-angiogenesis therapy is that angiogenesis inhibitors must be administered continuously to keep tumor vessels in check. The metal particle/irradiation approach need only be applied once or a limited number of times, since malignant cells are not just suppressed, but killed.

The enhanced radiotherapy methods of the present invention are also advantageous over boron neutron capture therapy (BNCT). In BNCT, a boron-10 containing agent is administered which will localize in the tumor. Neutrons are then applied to fission the boron, producing particles that may kill cells. BNCT has a number of disadvantages. For example, it requires a nuclear reactor to produce neutrons. Furthermore, boron-10 fission products only have an activity range of ~5 microns, whereas irradiated metal particles may affect cells 100 microns away or farther and thus would not require that every cell be sufficiently loaded with the agent.

Nevertheless, according to the present invention, the enhanced radiotherapy method disclosed herein can be used in conjunction with other existing therapies, such as chemotherapy, anti-angiogensis therapy and BNCT, as described hereinabove.

The present invention is further illustrated, but not limited by the following examples.

EXAMPLE 1

High Loading of Immunotargeted Gold Nanoparticles into Tumor Cells by Receptor Mediated Endocytosis An anti-Epidermal Growth Factor receptor (EGFr) antibody, MAb225, was expressed in cell culture, then purified by protein A column chromatography. This antibody has been shown to have good tumor to non-tumor localization of drug and radioisotope conjugates. The antibody was checked for purity by gel electrophoresis and its activity was verified by targeting to A431 cells using 15 nm colloidal gold antibody conjugates and silver enhancement. A431 cells, which highly express EGFr, and a control cell line with low expression of EGFr, MCF7, were cultured. Gold-antibody conjugates were added to the growth medium and 2 days later, the medium was changed and more gold-antibody was added. The uptake of colloidal gold by A431 cells was obvious after one day, since a cell pellet now had a black appearance, and examination under the light microscope revealed visible black dots in the cytoplasm. Targeting was specific since the control cell line did not show any visible uptake. On the fifth day, A431 cells were highly loaded with gold. No differences in cell growth were observed between cells exposed to and not exposed to gold.

The amount of gold uptake into the cells was quantified by atomic absorption spectroscopy. A431 cells after the above regimen contained 0.55% gold by weight. Such a level would be enough to have a major effect on the absorbed x-ray dose.

EXAMPLE 2

Dose Enhancement Factor of 4.5 Achieved in Vitro

A431 cells were targeted with the gold nanoparticle-anti-EGFr antibody conjugate as described in Example 1. The cells were then washed several times and resuspended in fresh medium, then aliquots of cell suspension were exposed to 250 kVp x-rays with doses between 0 and 16 Gray. A431 cells not exposed to gold nanoparticles were similarly irradiated and used as controls. After irradiation, cells were plated and grown for one week. A metabolic cell viability test was then done to determine the surviving fraction. Cells containing gold showed lower survival at all doses. Analysis of the data showed that the dose required to kill one-half of the cells was 4.5 times less for cells containing the gold nanoparticles. The dose enhancement factor was therefore 4.5.

EXAMPLE 3

Toxicity of Gold Nanoparticle Found to be Low

Balb/C mice with hindleg tumors were intravenously injected in the tail vein with gold nanoparticles with an average gold diameter of about 2 nm to produce a concentration in the tumor of approximately 0.3% or 0.15% gold by weight. After two weeks necropsy was performed which showed no unusual findings. Blood was drawn for hematology and chemistry, and yielded the results shown in Table 1. These preliminary results indicate there was no acute toxicity at these doses.

EXAMPLE 4

Gold Nanoparticles Found to have Higher Concentration in Tumors than Surrounding Non-tumor Tissue with Longer Residence Time Balb/C mice were implanted in their hindleg with the syngeneic mouse mammary tumor EMT-6. Gold nanoparticles 0.8 to 3 nm were injected intravenously into the tail vein, and the biodistribution of gold was followed by taking x-ray images at various time points. In addition, some animals were killed at these time points and their tissues analyzed by atomic absorption for gold content. Gold in the blood peaked at about 3–5 minutes, with a half-life of about 16 minutes. Muscle gold content peaked at about 3–5 minutes, with a half-life of about 21 minutes. Tumor had maximum gold at about 8 min, with a half-life of about 33 minutes. Therefore, a significant finding was that with these gold nanoparticles, muscle behaved similarly to the blood, indicating little extravasation into the muscle, whereas tumor had longer gold residence time indicating extravasation or binding. Another significant finding was that at all times measured, there was more gold in the tumor than muscle.

TABLE 1

| | | | | | | | | | | | | | | |
|---|---|---|---|---|---|---|---|---|---|---|---|---|---|---|
| Blood test results showing no toxicity. | | | | | | | | | | | | | | |
| Tumor Conc. of Au (approx) | Hgb (g/dl) | HCT | GLUCm (mg/dl) | CREm (mg/dl)-creatinine | BUNm (mg/dl) | TPm (g/dl)-total protein | ALBm (g/dl) | PHOSm (mg/dl) | TBIL (mg/dl) | DBILm (mg/dl) | GGT (IU/L) | AST (IU/L) | ALT (IU/L) | ALP (IU/L) |
| 0.30% | 13.8 | 40.0 | 213.0 | 0.3 | 25.0 | 4.1 | 1.3 | 7.9 | 0.4 | 0.1 | <5 | 67.0 | 27.0 | 50.0 |
| 0.30% | nd | nd | 272.0 | 0.3 | 22.0 | 4.2 | 1.4 | 6.8 | 0.3 | 0.1 | <5 | 95.0 | 32.0 | 55.0 |
| 0.15% | 14.6 | 42.5 | 276.0 | 0.3 | 22.0 | 4.4 | 1.5 | 7.6 | 0.0 | 0.1 | <5 | 62.0 | 28.0 | 48.0 |
| 0.15% | 14.1 | 41.3 | 238.0 | 0.2 | 24.0 | 4.0 | 1.4 | 7.7 | 0.1 | 0.1 | <5 | 64.0 | 25.0 | 48.0 |
| 0 (Control) | 14.7 | 42.2 | 253.0 | 0.3 | 20.0 | 3.9 | 1.3 | 7.3 | 0.3 | 0.1 | <5 | 54.0 | 23.0 | 51.0 |
| 0 (Control) | 15.3 | 44.1 | 251.0 | 0.3 | 24.0 | 4.3 | 1.4 | 6.3 | 0.2 | 0.1 | <5 | 71.0 | 25.0 | 59.0 |
| 0 (Control) | 13.4 | 38.3 | 227.0 | 0.3 | 28.0 | 4.1 | 1.4 | 6.1 | 0.1 | 0.1 | <5 | 80.0 | 22.0 | 50.0 |
| 0 (Control) | 13.8 | 40.0 | 266.0 | 0.2 | 20.0 | 3.8 | 1.3 | 6.6 | 0.2 | 0.1 | <5 | 81.0 | 24.0 | 46.0 |
| Normal mouse | 10.2–16.5 | 39–169 | NA | 0.2–0.9 | 8–32 | 3.5–7.2 | 2.5–3.0 | 5.7–9.2 | 0.0–0.9 | NA | NA | 54–298 | 17–77 | 35–96 | nd = not done due to lack of blood volume;
NA = not available.

Mice were killed at various time points after gold injection and tissues analyzed for gold content by graphite furnace atomic absorption spectroscopy. At 5 minutes after injection, the bulk tumor contained an average of 14 mg gold per gram of tumor (1.4% gold by weight), and muscle contained 2.6 mg gold per gram of muscle. The data are depicted in FIG. 1. These data demonstrated a tumor to non-tumor (muscle) ratio of gold to be 5.4. The data also demonstrated that therapeutic levels of gold can be delivered to tumors without any noticeable toxicity.

EXAMPLE 5

86% Tumors Cured with Gold Nanoparticles+Radiation Compared to 20% Cured with Radiation Alone Balb/C mice were implanted in their hindleg with the syngeneic mouse mammary tumor EMT-6. When tumors grew to about 60 mm$^3$, gold nanoparticles of about 2 nm in diameter were injected intravenously into the tail vein. 0.2 ml gold nanoparticle solution was injected so as to produce approximately 30 mg Au/ml or 15 mg Au/ml in the blood. Mouse legs with tumors were then irradiated 2 to 4 minutes after injection using a Siemens Stabilipan operating at 250 kVp with Thoraeus I filter delivering 26 gray (Gy) to the mouse tumors in approximately 4 minutes. Control mice received the same dose to their ipsilateral legs without gold injection, while other control mice with tumors received neither radiation nor gold.

Figure 2:
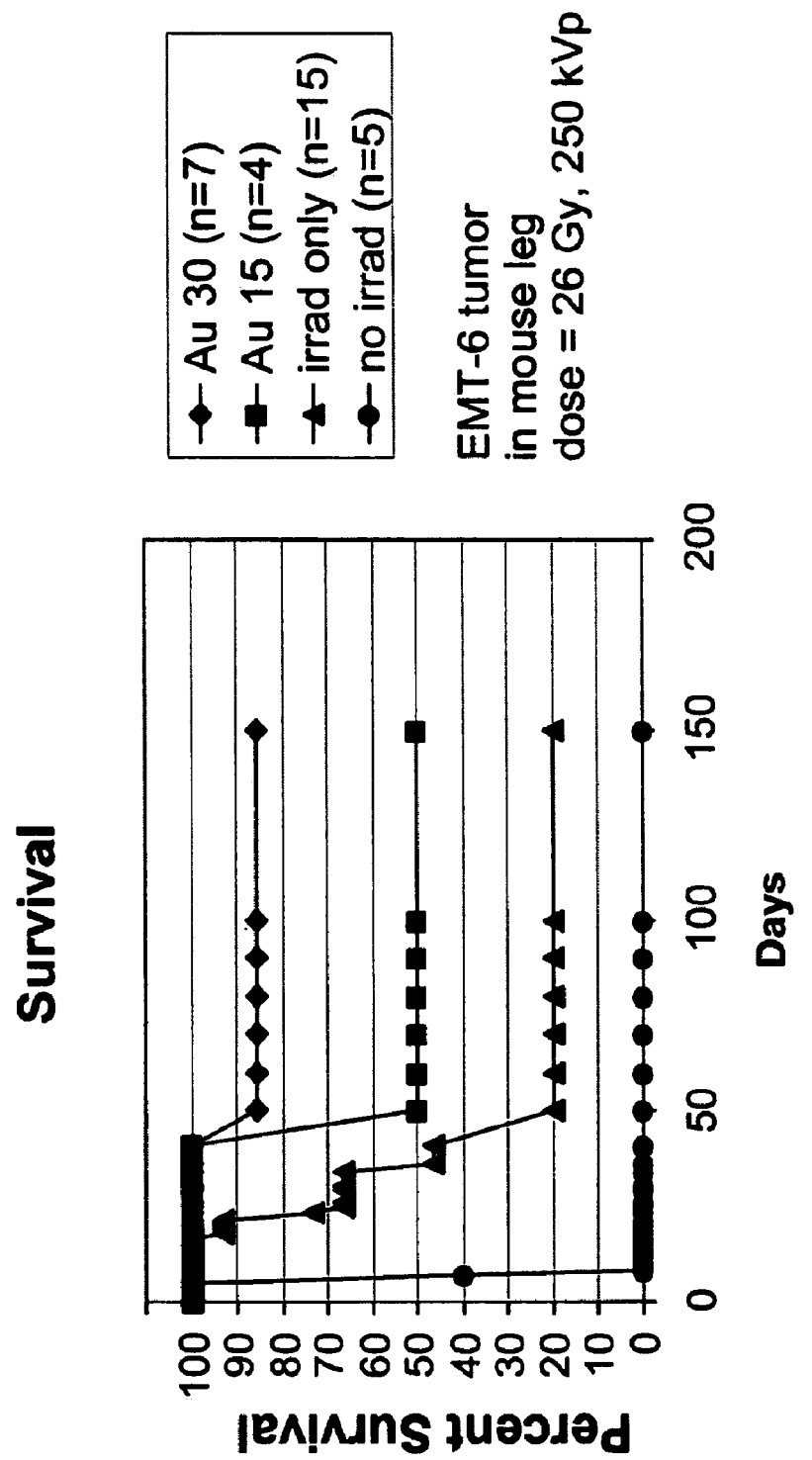
FIG. 2. Survival of mice with EMT6 syngeneic mammary tumors. Balb/C mice were injected subcutaneously with EMT6 tumor cells, and after the tumors grew to about 60 $mm^3$, some were injected with gold and irradiated with26 gray from a 250 kVp x-ray generator. Mice receiving no radiation died in about 1 week, or their tumors grew to be >500 $mm^3$ and they were euthanized. Those receiving radiation but no gold mostly died within 1 month, but 20% survived long term. Animals receiving the "15" dose of gold nanoparticles intravenously (corresponding to about 15 mg Au/ml initial blood concentration) showed 50% long-term survival. Animals that survived long term had tumors that shrunk and were no longer detectable. Animals receiving twice the amount of gold, "30", plus radiation, showed 86% long-term survival.

The results are depicted in FIG. 2. Mice receiving no irradiation (n=5) all died or had to be euthanized due to tumor overgrowth by 1 week. Of those that received radiation but not gold (n=15), 80% died between days 18 and 50 post irradiation, but a few (20%) survived long-term (>200 days), with no sign of tumors. Of those that received approximately 15 mg Au/ml in the blood plus radiation, 50% died between days 41 and 50, and 50% survived long-term without sign of tumor. Of those that received approximately 30 mg Au/ml in the blood plus radiation, 1 animal died on day 50, but the rest (86%) survived long-term without sign of tumor. In animals that survived, the tumors shrank and disappeared. Irradiated legs in survivors were functional and no difference was noticeable between those with or without gold. The gold nanoparticles therefore exhibited a clear gold-related dose response, in that those receiving more gold had better outcomes, and those receiving no gold clearly had the worst outcomes.

Combining the 25 and 50 mg Au/ml data, Wilcoxon non-parametric two-sample rank-sum analysis showed that the "gold+radiation" group had a better outcome than did the "radiation only" group with a certainty of >99% (p<0.01), thus proving statistical significance. Using the higher amount of gold, the tumor cure rate was over 4-fold greater (86% vs. 20%) by injecting gold than not injecting it prior to irradiation.

EXAMPLE 6

Immunotargeting of Metal Nanoparticles

Gold nanoparticles were covalently attached to Fab' antibody fragments or IgG and were shown to target antigen on blots. 100 ng mouse IgG was spotted onto nitrocellulose, and buffer only was spotted as a control. After drying, membranes were blocked with 4% bovine serum albumin, washed, then incubated with gold nanoparticles that had goat anti-mouse Fab' attached. After washing, blots were developed with silver enhancer. A dense spot only appeared at the target antigen location, indicating specific immuno-targeting of gold particles.

Gold nanoparticles were covalently attached to Fab' antibody fragments or IgG and were shown to specifically target antigens on tissue sections.

Gold particles were attached to anti-epidermal growth factor receptor (α-EGFr) antibody and injected intravenously into mice which had an A431 tumor implanted in the leg. Concentration of gold in various tissues was measured by atomic absorption as shown in Table 2.

TABLE 2

Summary table of gold biodistributions.

| | Blood % id/g | Muscle % id/g | Tumor % id/g | tumor/ muscle |
|---|---|---|---|---|
| 15 nm 24 hr | 0.060 ± 0.022 | 0.082 ± 0.047 | 0.65 ± 0.44 | 7.91 |
| 15 nm 96 hr | 0.019 ± 0.003 | 0.046 ± 0.022 | 0.08 ± 0.03 | 1.77 |
| 15 nm 3 × 0.5 ml | 0.014 ± 0.002 | 0.024 ± 0.001 | 0.19 ± 0.08 | 8.06 |
| 3 nm 24 hr | 4.51 ± 5.35 | 0.376 ± 0.158 | 2.31 ± 2.48 | 6.14 |
| 1.4 nm 24 hr | 6.59 ± 4.82 | 1.476 ± 0.181 | 5.10 ± 3.97 | 3.45 |

Notes:
All administrations were i.v.(0.2 ml), except the "15 nm 3 × 0.5 ml" sample, which was the same material as the 15 nm samples, but was 4 times more concentrated and injections were repeated on 3 different days. (% id/g = % injected dose per g tissue). Attachment of antibody to 3 and 15 nm gold was by adsorption, whereas attachment to 1.4 nm gold was covalent.

These results show specific targeting of gold nanoparticles to a tumor compared to surrounding non-tumor type tissue (muscle). A maximum tumor-to-non-tumor ratio of 8.06 was achieved.

EXAMPLE 7

Preparation of Tungsten Heteropolyanions Complexed with Quaternary Ammonium Salts and Reduced Toxicity in vivo.

A column containing carboxymethyl cellulose medium was prepared and charged with tetramethylammonium acetate, then rinsed with deionized water. Silicotungstic acid ($H_4SiW_{12}O_{40} \cdot 30H_2O$, 10 mg/ml in water) was injected onto the column and ion exchanged to produce the cluster surrounded and charge-shielded by quaternary ammonium ions. This complex was injected intravenously into CD1 outbred mice, which showed no adverse clinical signs, and continued to gain weight normally.

A complex between the quaternary cation, tetramethylammonium was also formed by mixing equimolar amounts of $H_4SiW_{12}O_{40} \cdot 30H_2O$, 10 mg/ml in water and tetramethylammonium bromide, 100 mg/ml in water. Some white precipitate was formed that was removed by centrifugation at 13 k×g for 10 minutes, then filtering through a molecular filter, Amicon Centricon 30, that only passes molecules less than 30,000 Daltons. A spectrum of the filtrate revealed a peak at 264 nm, indicitave of the $W_{12}$ complex, and showed little loss from the starting material. Dilutions were prepared and injected into CD1 mice. Good tolerance and normal weight gain was found at blood concentrations of approximately 5 mg/ml, whereas the uncomplexed heteropolytungstate was lethal at 1 mg/ml.

What is claimed is:

1. A method of enhancing the effects of radiation directed to a tissue or a population of cells in an animal comprising administering an amount of metal nanoparticles to said animal wherein the size of the metal cores of said nanoparticles is in the range of 0.8 to 400 nm in diameter, and subsequently irradiating the animal with radiation directed to said tissue or said population of cells wherein said radiation is in the form of x-rays of about 1 KeV to about 25.000 KeV.

2. A method of ablating a tissue or a population of cells in an animal comprising administering an amount of metal nanoparticles to said animal wherein the size of the metal cores of said nanoparticles is in the range of 0.8 to 400 nm in diameter, and subsequently irradiating the animal with radiation directed to said tissue or said population of cells wherein said radiation is in the form of x-rays of about 1 KeV to about 25.000 KeV.

3. The method of claim 1 or 2, wherein said animal is human.

4. The method of claim 1 or 2, wherein said tissue or said population of cells is tumor.

5. The method of claim 4, wherein said tumor is a solid tumor selected from the group consisting of carcinomas, brain tumor, melanomas, lymphomas, plasmocytoma, sarcoma, glioma and thymoma.

6. The method of claim 4, wherein said tumor is myeloma, leukemia, or a tumor of oral cavity, pharynx, digestive system, respiratory system, bones, joints, soft tissue, skin, breast, genital system, urinary system, eye, orbit, the nervous system, or endocrine system.

7. The method of claim 1 or 2, wherein said metal nanoparticles comprise at least one heavy metal selected from the group consisting of gold, silver, platinum, palladium, cobalt, iron, copper, tin, tantalum, vanadium, molybdenum, tungsten, osmium, iridium, rhenium, hafiuium, thallium, lead, bismuth, gadolinium, dysprosium, holmium, and uranium.

8. The method of claim 7, wherein said metal nanoparticles comprise at least gold.

9. The method of claim 7, wherein said nanoparticles comprise at least two heavy metals from said group.

10. The method of claim 1 or 2, wherein the size of the metal cores of said metal particles is 0.8–3 nm and wherein said metal is gold.

11. The method of claim 1 or 2, wherein said metal nanoparticles comprise a surface layer material.

12. The method of claim 11, wherein said surface layer material comprises a molecule comprising a sulfur, phosphorus or amine group.

13. The method of claim 12, wherein said molecule is thioglucose.

14. The method of claim 11, wherein said surface layer material is a molecule selected from the group consisting of a synthetic polymer, a peptide or polypeptide, an antibody or a fragment thereof, a nucleic acid, a carbohydrate molecule, a lipid molecule, a drug and synthetic molecule.

15. The method of claim 1 or 2, wherein said nanoparticles are polyanions of metals complexed with quaternary ammonium salts for use in radiation enhancement.

16. The method of claim 1 or 2, wherein said metal nanoparticles comprises a targeting molecule, wherein said targeting molecule binds specifically to molecules localized within said tissue or said population of cells.

17. The method of claim 16, wherein said targeting molecule is a peptide or an antibody.

18. The method of claim 16, wherein said tissue or said population of cells is tumor and said targeting molecule binds specifically to angiogenic molecules in the endothelium of said tumor.

19. The method of claim 1 or 2, wherein said metal nanoparticles are administered to said animal by intravenous or intra-aretrial injection, direct injection into said tissue or population of cells, implantation of a device capable of a slow release of said metal nanoparticles, or injection into a body cavity.

20. The method of claim 1 or 2, wherein said metal nanoparticles are administered to said animal in an amount to achieve a concentration in said tissue or said population of cells in the animal of at least about 0.1% metal by weight.

21. A method of ablating a population of cells from a tissue in an animal comprising removing said tissue from said animal, admixing an amount of metal nanoparticles with said tissue ex vivo wherein said metal nanoparticles bind specifically to said population of cells, and irradiating said tissue to ablate said population of cells.

22. The method of claim 21, wherein said animal is human.

23. The method of claim 21, wherein said tissue is blood, bone marrow or a lymphoid tissue.

24. The method of claim 21, wherein said metal nanoparticles comprise at least one heavy metal selected from the group consisting of gold, silver, platinum, palladium, cobalt, iron, copper, tin, tantalum, vanadium, molybdenum, tungsten, osmium, iridium, rhenium, hafnium, thallium, lead, bismuth, gadolinium, dysprosium, holmium, and uranium.

25. The method of claim 24, wherein said metal nanoparticles comprise at least gold.

26. The method of claim 21, wherein said nanoparticles comprise at least two heavy metals from said group.

27. The method of claim 21, wherein the size of the metal cores of said nanoparticles is in the range of 0.8 to 400 nm in diameter.

28. The method of claim 27, wherein the size of the metal cores is 0.8–3 nm and wherein said metal is gold.

29. The method of claim 21, wherein said metal nanoparticles comprise a surface layer material.

30. The method of claim 29, wherein said surface layer material comprises a molecule comprising a sulfur, phosphorus or amine group.

31. The method of claim 30, wherein said molecule is thioglucose.

32. The method of claim 29, wherein said surface layer material is a molecule selected from the group consisting of a synthetic polymer, a peptide or polypeptide, an antibody or a fragment thereof, a nucleic acid, a carbohydrate molecule, a lipid molecule, a drug and synthetic molecule.

33. The method of claim 21, wherein said nanoparticles are polyanions of metals complexed with quaternary ammonium salts for use in radiation enhancement.

34. The method of claim 21, wherein said metal nanoparticles comprises a targeting molecule, wherein said targeting molecule binds specifically to said population of cells.

35. The method of claim 34, wherein said targeting molecule is a peptide or an antibody.

36. The method of claim 21, wherein said metal nanoparticles are admixed with said tissue to achieve a concentration in the mixture of at least about 0.1% metal by weight.

37. The method of claim 21, wherein said radiation is in a form selected from the group consisting of x-rays, microbeam arrays of x-rays, radioisotopes, visible light, lasers, infrared, microwave, radio frequencies, ultraviolet radiation, electrons, protons, ion beams and neutrons.

38. The method of claim 37, wherein said radiation is in the form of x-rays of about 1 KeV to about 25,000 KeV.

39. The method of claim 21, wherein said population of cells are cancerous.

40. A method of enhancing the effects of radiation directed to a tissue or a population of cells in an animal comprising administering an amount of metal nanoparticles to said animal wherein the size of the metal cores of said nanoparticles is in the range of 0.8 to 400 nm in diameter, and subsequently irradiating the animal with radiation directed to said tissue or said population of cells, wherein said metal nanoparticles comprise a surface layer material which comprises thioglucose.

41. A method of ablating a tissue or a population of cells in an animal comprising administering an amount of metal nanoparticles to said animal wherein the size of the metal cores of said nanoparticles is in the range of 0.8 to 400 nm in diameter, and subsequently irradiating the animal with radiation directed to said tissue or said population of cells, wherein said metal nanoparticles comprise a surface layer material which comprises thioglucose.

42. The method of claim 40 or 41, wherein said tissue or population of cells is tumor.

43. The method of claim 40 or 41, wherein said metal particles comprise gold.

44. The method of claim 40 or 41, wherein the size of the metal cores of said metal particles is 0.8–3 nm.

45. The method of claim 40 or 41, wherein said radiation is in a form selected from the group consisting of x-rays, microbeam arrays of x-rays, radioisotopes, electrons, protons, ion beams and neutrons.

46. A method of enhancing the effects of radiation directed to a tissue or a population of cells in an animal comprising administering an amount of metal nanoparticles to said animal wherein the size of the metal cores of said nanoparticles is in the range of 0.8 to 400 nm in diameter, and subsequently irradiating the animal with radiation directed to said tissue or said population of cells, wherein said nanoparticles are polyanions of metals complexed with quaternary ammonium salts.

47. A method of ablating a tissue or a population of cells in an animal comprising administering an amount of metal nanoparticles to said animal wherein the size of the metal cores of said nanoparticles is in the range of 0.8 to 400 nm in diameter, and subsequently irradiating the animal with radiation directed to said tissue or said population of cells, wherein said nanoparticles are polyanions of metals complexed with quaternary ammonium salts.

48. A method of enhancing the effects of radiation directed to a tissue or a population of cells in an animal comprising administering an amount of metal nanoparticles to said animal wherein the size of the metal cores of said nanoparticles is in the range of 0.8 to 400 nm in diameter, and subsequently irradiating the animal with radiation directed to said tissue or said population of cells, wherein said metal nanoparticles are administered to said animal in an amount to achieve a concentration in said tissue or said population of cells in the animal of at least about 0.1% metal by weight.

49. The method of claim 46 or 47, wherein said tissue or population of cells is tumor.

50. A method of ablating a tissue or a population of cells in an animal comprising administering an amount of metal nanoparticles to said animal wherein the size of the metal cores of said nanoparticles is in the range of 0.8 to 400 nm in diameter, and subsequently irradiating the animal with radiation directed to said tissue or said population of cells, wherein said metal nanoparticles are administered to said animal in an amount to achieve a concentration in said tissue or said population of cells in the animal of at least about 0.1% metal by weight.

51. The method of claim 48 or 50, wherein said tissue or population of cells is tumor.

52. The method of claim 48 or 50, wherein said metal particles comprise gold.

53. The method of claim 48 or 50, wherein the size of metal cores of said metal particles is 0.8–3 nm.

54. The method of claim 48 or 50, wherein said radiation is in a form selected from the group consisting of x-rays, microbeam arrays of x-rays, radioisotopes, electrons, protons, ion beams and neutrons.

\* \* \* \* \*